US00PP14630P29

(12) United States Plant Patent
Voogt

(10) Patent No.: US PP14,630 P2
(45) Date of Patent: Mar. 23, 2004

(54) POINSETTIA PLANT NAMED 'FUTURE PINK'

(50) Latin Name: *Euphorbia pulcherrima*
Varietal Denomination: Future Pink

(75) Inventor: Eric Voogt, Langley (CA)

(73) Assignee: Florfis AG (CH)

( * ) Notice: Subject to any disclaimer, the term of this patent is extended or adjusted under 35 U.S.C. 154(b) by 0 days.

(21) Appl. No.: 10/382,657

(22) Filed: Mar. 7, 2003

(51) Int. Cl.[7] ..... A01H 5/00

(52) U.S. Cl. ..... Plt./306

(58) Field of Search ..... Plt./306, 303

*Primary Examiner*—Bruce R. Campell
*Assistant Examiner*—June Hwu
(74) *Attorney, Agent, or Firm*—Foley & Lardner

(57) ABSTRACT

A new and distinct Poinsettia plant named 'Future Pink', characterized as having relatively uniform, salmon-pink bract color; small to medium sized inflorescences with distinctly curled bracts; intense medium-green foliage with somewhat twisted leaf blade and with slightly undulated margins; moderately compact and well-branched, round plant habit; and medium to moderately late flowering response.

1 Drawing Sheet

Latin name of the genus and species of the plant claimed: *Euphorbia pulcherrima.*
Variety denomination: Future Pink.

BACKGROUND OF THE INVENTION

The present invention relates to a new and distinct cultivar of poinsettia plant known by the variety denomination 'Future Pink', and botanically known as *Euphorbia pulcherrima.*

'Future Pink' was derived from a naturally occurring mutation in the variety 'Future' (U.S. Plant patent application Ser. No. 09/590,012, abandoned), commercially known as 'Caroussel'.

The mutation was discovered by the inventor, Eric Voogt, in his greenhouse in Langley, British Columbia, Canada, in November, 2000, among a group of flowering plants. The plant was selected for its salmon-pink colored bracts. The plant was left to develop vegetative shoots, which were cut by the inventor and used for propagation (first asexual reproduction) in the spring of 2001. The resulting plants appeared uniform with respect to both the curling of the bracts and the salmon-pink bract color. This result was confirmed when the propagation and examination was repeated on a larger scale in the fall of 2002.

Horticultural examination of the clone starting in 2001 and continuing thereafter has demonstrated that the combination of characteristics as herein disclosed for 'Future Pink' are firmly fixed and retained through successive generations of asexual reproduction.

BRIEF SUMMARY OF THE INVENTION

The following traits have been repeatedly observed and are determined to be basic characteristics of 'Future Pink', which in combination distinguish this Poinsettia as a new and distinct cultivar:

1. Relatively uniform, salmon-pink bract color;
2. small to medium sized inflorescences with distinctly curled bracts;

3. intense medium-green foliage with somewhat twisted leaf blade and with slightly undulated margins;
4. moderately compact and well-branched, round plant habit; and
5. medium to moderately late flowering response.

'Future Pink' has not been observed under all possible environmental conditions. The phenotype may vary significantly with variations in environment such as temperature, light intensity, and day-length. Th following observations, measurements and comparisons describe plants grown in Hillscheid, Germany, under greenhouse conditions which approximate those generally used in commercial practice.

Of the many commercial cultivars known to the inventor, the most similar in comparison to 'Future Pink' is the parent cultivar 'Future', and the variety 'Winterrose Pink' (unpatented, Plant Breeder's Rights denomination 'Eckaddis').

'Future' is characterized by brilliant red colored bracts with wavy and curled margins, medium green foliage with somewhat wavy margins, and medium tall, round plant habit. In contrast to the scarlet-red flowered cultivar 'Future', 'Future Pink' has salmon-pink colored bracts. Furthermore, plant habit of 'Future Pink' is slightly smaller than that of 'Future'.

In comparison to 'Winterrose Pink', 'Future Pink' has clearly differently shaped bracts, which are horizontally or slightly upward directed. In contrast to that, the bracts of 'Winterrose-Pink' are incurved and downwards directed forming an almost closed, spherically shaped inflorescence. Furthermore, 'Future Pink' has a medium green foliage in contrast to the dark green foliage of 'Winterrose Pink'.

BRIEF DESCRIPTION OF THE DRAWING

The accompanying color photographic drawing shows typical inflor scence and foliag of 'Future Pink', with colors being as true as possibl with illustrations of this type. The photograph shows a mature potted plant.

DETAILED BOTANICAL DESCRIPTION

The plants described were grown in a greenhouse in Hillscheid, Germany, in the fall of 2002. Rooted cuttings were planted into 14 cm pots on July 25, and were pinched on August 8, leaving 7–8 leaves. Initially, the temperature was between a minimum of 19° C. and 24.5° C. maximum (ventilation temperature), and lower beginning October 1, minimum 16° C. to 23°. The plants initiated flowers under short-day conditions under natural short-day conditions in fall, no black cloth was applied. Observations and measurements were mainly taken in mid December, when the plants were in full flower and about 20 weeks old.

In the following description, color references are made to The Royal Horticultural Society Colour Chart (R.H.S.). The color values were determined indoors in a north light.

Plant:

*Form.*—Shrub, self-branching.

*Growth habit.*—Medium vigor, but relatively compact plant habit, well-branched pinched plants are bushy and round in shape.

*Height* (*above soil line*).—22.0 cm.

*Width.*—37.0 cm.

*Average number of branch s.*—9.

*Branch length.*—About 19–20 cm, branch diameter: 5–6 mm.

*Average number of inflorescence.*—8.

*Stem color.*—Green, RHS 137 D to light green, RHS 144 B, near tips, no visible anthocyanin.

*Internode length.*—15–20 mm.

*Rooting.*—Fast to medium, sufficiently rooted for transplanting after about 20–24 days in a greenhouse at a temperature of 22–24° C.

*Blooming habit.*—Begin under natural short day conditions in fall; botanically (cyathia open): around December 1, commercially (bracts colored, marketable): in early to mid-December.

*Flowering response time.*—About 10 weeks.

Foliage:

*Shape.*—Ovate, with mostly rounded to truncate bases, only very weak lobes, and acuminate tips.

*Margin.*—Mostly entire, somewhat wavy, occasionally with a few irregular notches.

*Texture.*—Upper surface: not completely flat, but often somewhat twisted, only weakly veined; lower surface: slightly protruding midrib and finer side veins in a pinnate patt rn.

*Vein coloration.*—Upper and low r surface pale light green, RHS 145 C.

*Leaf blade size.*—Length: 10.5 cm; average width 6.8 cm.

*Petiole.*—Length 3.5–4 cm.

*Quantity.*—About 55–65 leaves per plant.

*Color.*—Generally medium green, uniform. Mature foliage: upper surface, RHS 137 A; under surface, RHS 138 B. New foliage: upper side: RHS 144 A, partly 137 D; under side: RHS 143 C.

*Leaf petiole.*—Upper side: brownish-pink, near RHS 47 C; lower side: light green, RHS 144 B.

*Aspect.*—Petioles are horizontally or slightly upward directed, with the leaf blades held almost horizontally.

Disease resistance: No special observations made.

Flowering description:

*Whole inflorescence with surrounding bracts.*—A small to medium sized ring of relatively short, curled bracts which are horizontal to somewhat upward directed.

*Diameter.*—About 13.8 cm.

*Height.*—30–35 mm.

*Number of bracts per inflorescence.*—7–9 (size over 2 cm).

*Keeping quality.*—Good quality will be maintained for about 4 weeks at minimum, no drooping bracts, no fading.

Bracts:

*Shape.*—Mostly obovate, with acute base, no lobes, and acuminate tip.

*Size of the largest fully colored bract.*—7.5 cm long; 4.8 cm wide.

*Texture.*—Leaf blades appear curled, with strong undulation at the margins.

*Vein color.*—Upper side corresponds closely to bract color; lower side: pale green, RHS 150 D or cream, RHS 159 B.

*Color.*—Generally bright pink; upper surface mainly RHS 43 C, somewhat deeper near the midrib: near RHS 47 A, possibly lighter near margins of the lowest bracts: RHS 39 B; lower surface main part RHS 43 C, in the middle of the leaf often greenish, approx. RHS 145 A.

*Petiole.*—10–15 mm long; upper side color RHS 43 B; lower side pale light green 150 D.

*Cyme.*—15–18 mm in diameter, 7–10 cyathia borne in a tight cluster.

*Cyathium.*—Ovate, about 5 mm in diameter, medium to light green colored, RHS 143 B, top dull orange-pink, RHS 47 C.

*Peduncle.*—Light green, RHS 144 B, partly pink, RHS 47 C, about 4 mm long.

*Nectar cups.*—One or two per cyathium, about 3–5 mm wide, orange colored RHS 33 A to 33 B.

Reproductive organs:

*Stamens.*—Not always developed, about 10–15 in a cluster, filaments short, 2–3 mm, reddish, RHS 47 A; little to moderate pollen, yellow, RHS 12 A.

*Pistil.*—Style pink, RHS 51 B, and red stigma, RHS 46B, stigma trifurcate, 6-lobed.

*Ovaries.*—Light to medium green, RHS 143 B, initially obovate, initially 3 mm in diameter, 4–5 mm long, later larger and triangular, 3 ovules.

*Fruit/seed set.*—No seed set observed, but appears to be fertile.

I claim:

1. A new and distinct Poinsettia plant named 'Future Pink' as illustrated and described herein.

* * * * *

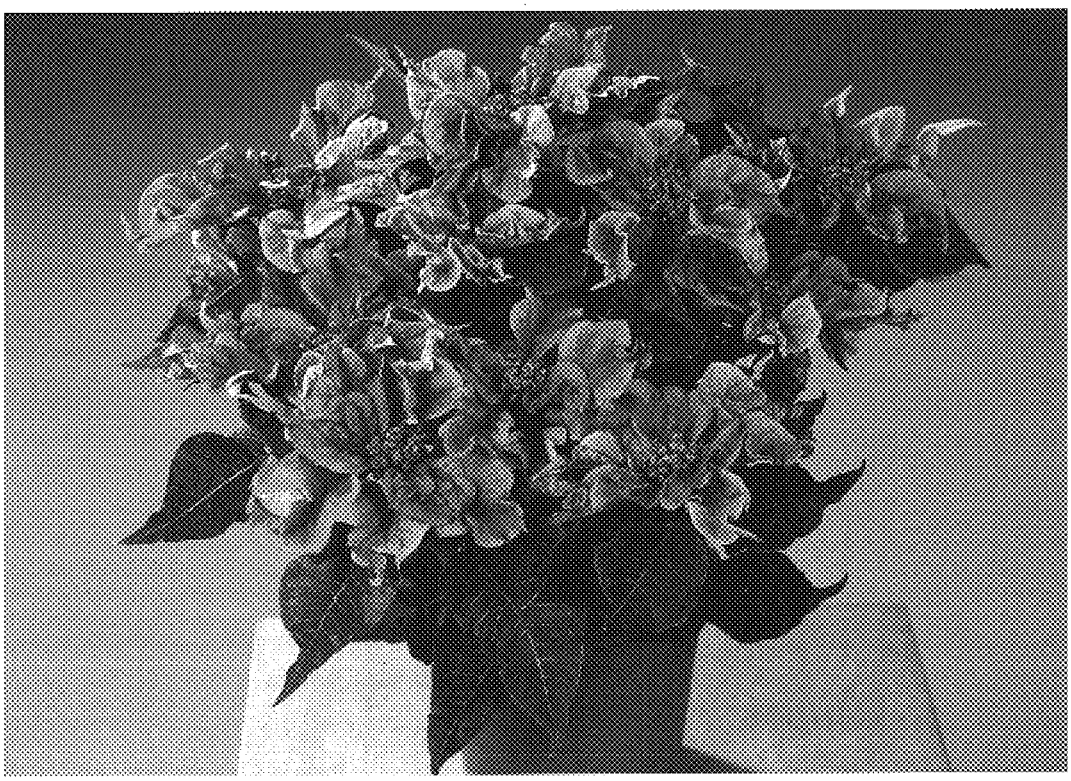

UNITED STATES PATENT AND TRADEMARK OFFICE

CERTIFICATE OF CORRECTION

PATENT NO. : PP 14,630 P2
DATED : March 23, 2004
INVENTOR(S) : Eric Voogt

It is certified that error appears in the above-identified patent and that said Letters Patent is hereby corrected as shown below:

Title page,
Item [73], delete Assignee.

Signed and Sealed this

Twenty-seventh Day of December, 2005

JON W. DUDAS
*Director of the United States Patent and Trademark Office*